United States Patent
Distasi et al.

(10) Patent No.: US 9,763,573 B2
(45) Date of Patent: Sep. 19, 2017

(54) SYSTEM AND METHOD FOR USING MICROSACCADE PEAK VELOCITY AS A MEASURE OF MENTAL WORKLOAD AND FATIGUE

(71) Applicants: Leandro Luigi Distasi, Phoenix, AZ (US); Stephen L. Macknik, Anthem, AZ (US); Susana Martinez-Conde, Anthem, AZ (US)

(72) Inventors: Leandro Luigi Distasi, Phoenix, AZ (US); Stephen L. Macknik, Anthem, AZ (US); Susana Martinez-Conde, Anthem, AZ (US)

(73) Assignee: Dignity Health, San Francisco, CA (US)

( * ) Notice: Subject to any disclaimer, the term of this patent is extended or adjusted under 35 U.S.C. 154(b) by 245 days.

(21) Appl. No.: 14/359,255

(22) PCT Filed: Nov. 23, 2012

(86) PCT No.: PCT/US2012/066461
§ 371 (c)(1),
(2) Date: May 19, 2014

(87) PCT Pub. No.: WO2013/078461
PCT Pub. Date: May 30, 2013

(65) Prior Publication Data
US 2015/0029462 A1    Jan. 29, 2015

Related U.S. Application Data

(60) Provisional application No. 61/562,576, filed on Nov. 22, 2011.

(51) Int. Cl.
*A61B 3/113*    (2006.01)
*A61B 5/00*    (2006.01)
(Continued)

(52) U.S. Cl.
CPC .............. *A61B 3/113* (2013.01); *A61B 5/16* (2013.01); *A61B 5/165* (2013.01); *A61B 5/18* (2013.01); *A61B 5/7246* (2013.01)

(58) Field of Classification Search
CPC .................................. A61B 3/113; A61B 5/00
See application file for complete search history.

(56) References Cited

U.S. PATENT DOCUMENTS

| 5,382,989 A | 1/1995 | Uomori et al. |
| 2008/0188777 A1 | 8/2008 | Bedziouk et al. |

(Continued)

FOREIGN PATENT DOCUMENTS

WO    2011-055505 A1    5/2011

OTHER PUBLICATIONS

Bahill, A. Terry, and Lawrence Stark. "Overlapping Saccades and Glissades Are Produced by Fatigue in the Saccadic Eye Movement System." Experimental Neurology 48 (1975): 95-106. Print.*

(Continued)

*Primary Examiner* — Zachary Wilkes
(74) *Attorney, Agent, or Firm* — Quarles & Brady LLP

(57) ABSTRACT

A system and method for determining a subject's level of fatigue. The method includes measuring microsaccadic eye movement dynamics of the subject, calculating a current microsaccade peak velocity from the measured microsaccadic eye movement dynamics, and comparing the current microsaccade peak velocity to a baseline microsaccade peak velocity. The method further includes determining the level of fatigue based on a difference between the current microsaccade peak velocity and the baseline microsaccade peak velocity.

14 Claims, 5 Drawing Sheets

(51) Int. Cl.
*A61B 5/16* (2006.01)
*A61B 5/18* (2006.01)

(56) References Cited

U.S. PATENT DOCUMENTS

| | | |
|---|---|---|
| 2009/0198148 A1 | 8/2009 | Lonky |
| 2009/0312665 A1 | 12/2009 | Daimoto et al. |
| 2010/0039617 A1 | 2/2010 | Martinez-Conde et al. |
| 2010/0191156 A1 | 7/2010 | Sakamoto et al. |
| 2010/0277693 A1 | 11/2010 | Martinez-Conde et al. |

OTHER PUBLICATIONS

Rolfs, Martin. "Microsaccades: Small Steps on a Long Way." Vision Research 49 (2009): 2415-441. Print.*

Engbert, Ralf. "Microsaccades: A microcosm for research on oculomotor control, attention, and visual perception." Progress in brain research 154 (2006): 177-192.*

Zils, Elizabeth; et al. "Differential Effects of Sleep Deprivation on Saccadic Eye Movements." Sleep 28.9 (2005): pp. 1109-1115. Print.*

International Search Report and Written Opinion under date of Sep. 29, 2014 in connection with PCT/US2014/035082.

International Search Report and Written Opinion under date of Feb. 8, 2013 in connection with PCT/US12/066461.

* cited by examiner

SYSTEM AND METHOD FOR USING MICROSACCADE PEAK VELOCITY AS A MEASURE OF MENTAL WORKLOAD AND FATIGUE

CROSS-REFERENCE TO RELATED APPLICATIONS

This application represents the national stage entry of PCT International Application No. PCT/US2012/066461 filed Nov. 23, 2012, which claims the benefit of U.S. Provisional Patent Application Ser. No. 61/562,576, filed on Nov. 22, 2011, the disclosures of which are incorporated herein by reference in their entirety for all purposes.

BACKGROUND OF THE INVENTION

The present application is directed to monitoring eye movements to determine a subject's level of fatigue and/or mental workload. In particular, the present application is directed to analyzing microsaccade peak velocity relative to a baseline value to measure a subject's level of fatigue and/or mental workload with respect to time on a task or complexity of a task.

Air traffic control (ATC) operators perform demanding visual search tasks, in which the consequences of impaired performance due to mental fatigue and/or cognitive overload are severe. In particular, decreased attentional levels can cause operators to misread or ignore incoming information, which compromises safety and job performance. Numerous studies have focused on assessing and/or improving ATC work conditions, and regulations have been set to increase staff numbers and decrease work hours, but fatigue-related incidents continue to occur. Thus, there is a great need to monitor mental state in real-time in complex systems such as ATC towers, where the combination of long duty periods, insufficient sleep, monotonous tasks, and high stress leads to physical and mental operator fatigue.

SUMMARY OF THE INVENTION

The present invention provides a method for determining a subject's level of fatigue. The method includes measuring microsaccadic eye movement dynamics of the subject, calculating a current microsaccade peak velocity from the measured microsaccadic eye movement dynamics, and comparing the current microsaccade peak velocity to a baseline microsaccade peak velocity. The method further includes determining the level of fatigue based on a difference between the current microsaccade peak velocity and the baseline microsaccade peak velocity.

A system in accordance with the present invention includes a system configured to receive a measure of microsaccadic eye movement dynamics of the subject and a computer readable storage medium. The computer readable storage medium has stored thereon instructions that, when executed by a computer processor, cause the processor to determine, using the measure of microsaccadic eye movement dynamics of the subject, a current microsaccade peak velocity, compare the current microsaccade peak velocity to a stored baseline microsaccade peak velocity, and generate a report indicating the subject's level of fatigue based on a difference between the current microsaccade peak velocity and the stored baseline microsaccade peak velocity.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6b is a graphical representation relating saccade peak velocity slope to time on a task involving the moving saccade of FIG. 6a.

FIG. 6c is a graphical representation relating microsaccade peak velocity slope to time on a task involving the moving saccade of FIG. 6a.

DETAILED DESCRIPTION OF THE INVENTION

The present invention generally provides a method of monitoring eye movements of a subject to measure the subject's level of fatigue and/or mental workload performing a task. Such eye movements can include microsaccade dynamics, and more specifically, microsaccade peak velocity. The literature rules out other instantiations of microsaccade velocity, such as mean velocity, as too unreliable. The microsaccade peak velocity can be compared to a baseline value to determine how variables such as time-on-task or task complexity affect the subject's level of fatigue or mental workload. In particular, microsaccade peak velocity decreases from the baseline value during fatigue and/or mental workload, and this decrease can be monitored to generate reports regarding a subject's fatigue level or mental workload. This method can serve as an objective measurement of fatigue and/or mental workload because, as further discussed below, microsaccades are involuntary movements that are not, generally, perceived by the subject, thus they do not know when they are making microsaccades.

Figure 1:
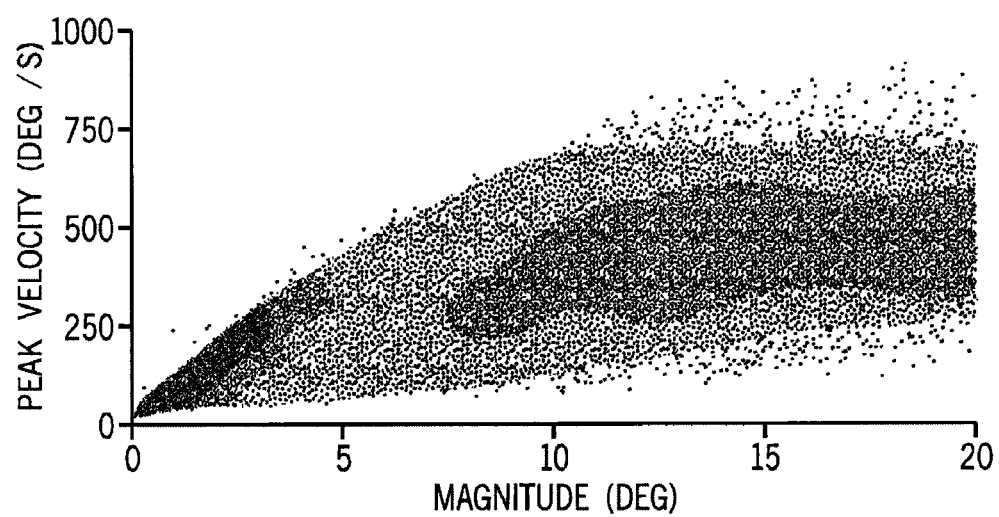
FIG. 1 is a graphical representation of saccade peak velocity as a function of saccade magnitude, illustrating a saccade main sequence.

Eye movements are essential for visual perception. For example, high-resolution information crucial to many everyday tasks is available only in the fovea, which subtends just 0.1% of the visual field. Therefore, fast ballistic eye movements called "saccades" turn the eye 1-3 times each second to bring successive regions of interest in the visual onto the fovea. Saccades are critical to navigating the visual world, to reading and interacting with objects, and to performing demanding visual monitoring tasks such as air traffic or nuclear platform control. Saccadic eye movements vary in amplitude, duration, and velocity, and saccadic mean velocity, peak velocity, and duration all increase as a function of saccadic amplitude, a relationship known as the "main sequence," as shown in FIG. 1 (with respect to peak velocity as a function of saccadic amplitude). In addition, a subject's eyes move constantly even when they try to fixate their gaze. These fixational saccades that occur during gaze fixation, called "microsaccades," also lie on the saccadic main sequence.

Identification, characterization, and measurement of eye movements can be useful for determining various aspects of attention and neural disease. For example, certain kinds of traceable eye movements can be analyzed as clear indices of attentional state. Thus, in accordance with the present invention, alterations in attentional state, such as those induced by mental fatigue and task complexity, may be detectable non-invasively using eye movement analysis.

Figure 2:
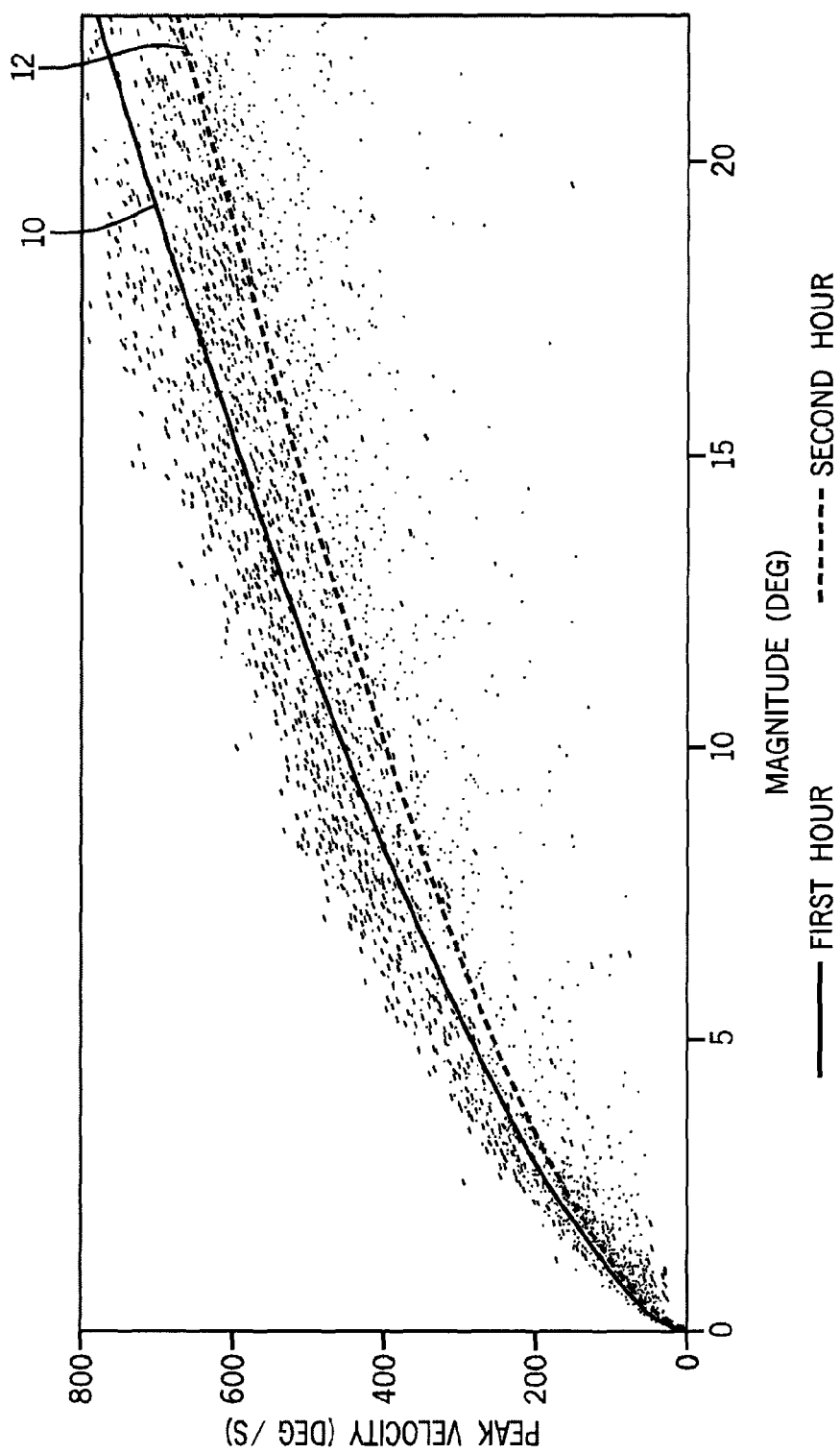
FIG. 2 is a graphical representation of saccade peak velocity as a function of saccade magnitude after a first hour of performing a task and after a second hour of performing a task.

In particular, it has been identified that eye movement dynamics—large voluntary saccades—degrade as a function of mental fatigue. FIG. 2 illustrates this link by showing a first main sequence after one hour of performing an air traffic control task, and a second main sequence after two hours of performing the air traffic control task. Saccadic peak velocity, measured as a slope of the regression line fitting each main sequence population (10 indicating the regression line of the first sequence, and 12 indicating the regression line of the second sequence) is shown to decrease between the first hour to the second hour. In other words, saccadic peak velocity decreases with time-on-task (TOT). Furthermore, saccadic peak velocity may also decrease with task complexity.

While this link has currently only been identified with large voluntary saccades, it can also apply to involuntary microsaccades. Thus, the present invention can provide a method for measuring saccades of all types, including microsaccades, as a function of mental fatigue and/or task complexity in a task by continuously measuring eye movement dynamics. In some applications, microsaccades may have the advantage over other types of saccades because they are involuntary and a subject does not know that they are making them, despite that they are clearly detectable on eye movement traces from multiple types of eye position measurement devices. As such, microsaccade dynamics may be an objective physiological measure of cognitive workload, when compared against a baseline measure, because the observer cannot fake the result. Measurements of microsaccades in accordance with the present invention, combined with saccadic measures, can thus generate an objective measure of cognitive workload. Furthermore, this can be done through online real-time analysis, as further described below.

Figure 3:
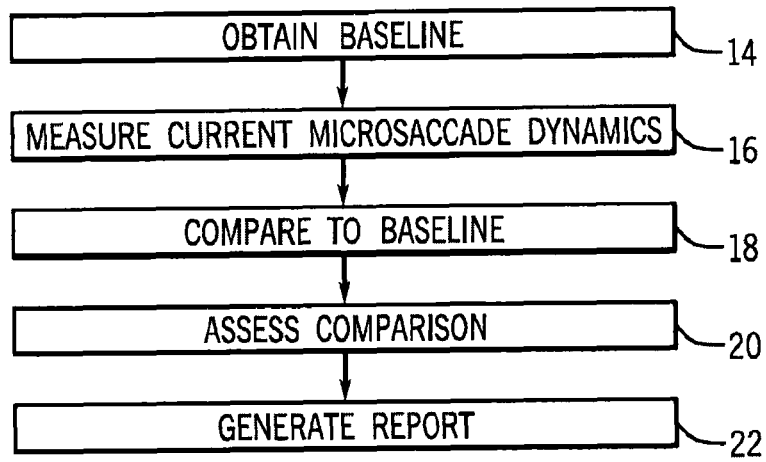
FIG. 3 is a flow chart setting forth the steps of a method for determining level of fatigue and/or mental workload, in accordance with the present invention.
Figure 4:
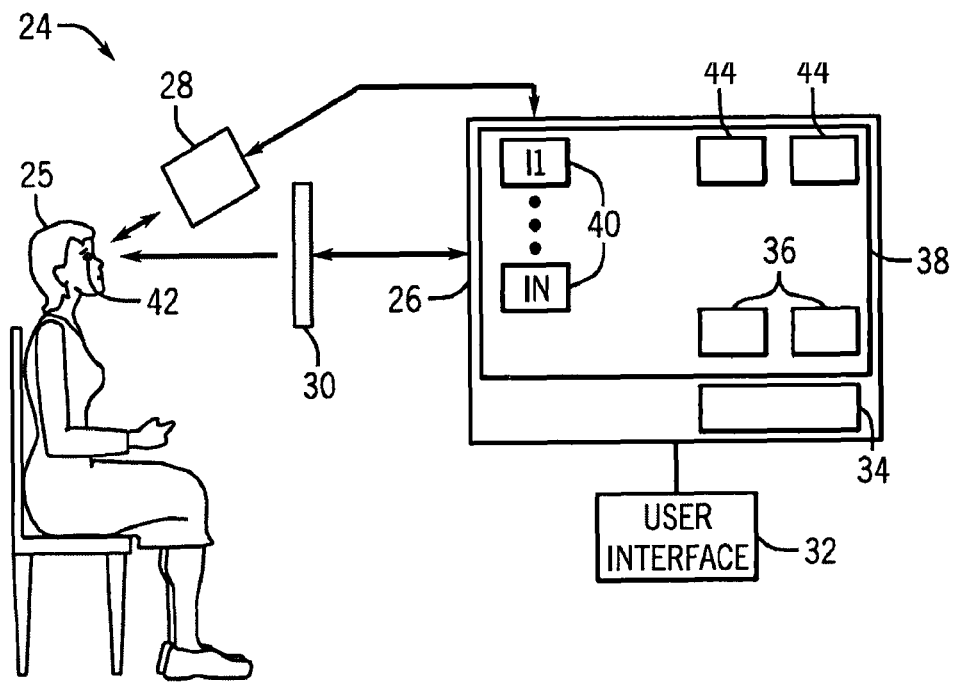
FIG. 4 is a schematic view of a system according to the present invention.
Figure 5:
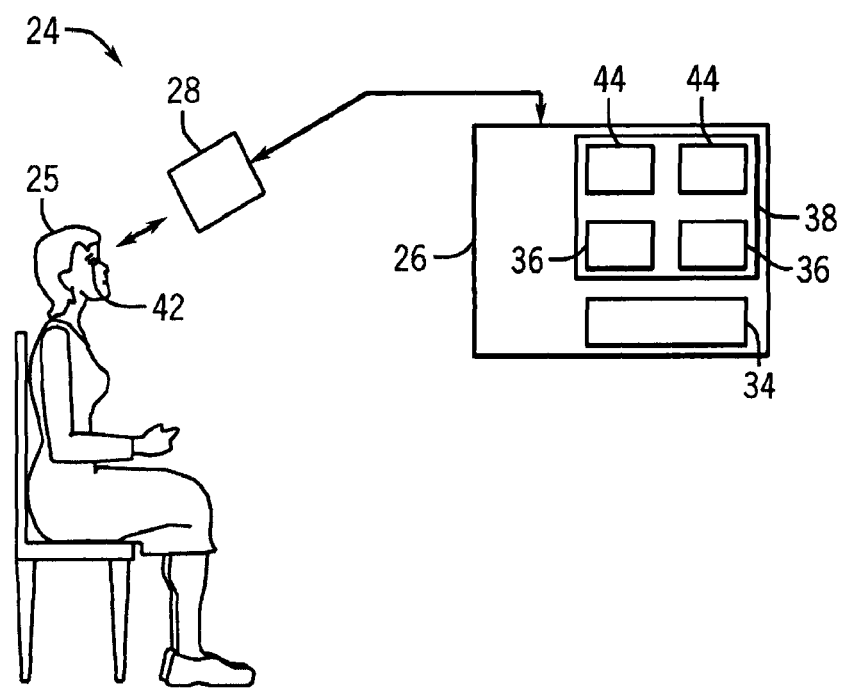
FIG. 5 is a schematic view of another system according to the present invention.

In light of the above, a method for non-invasively measuring mental workload and fatigue, in accordance with the present invention, is illustrated in FIG. 3. The present invention further provides systems for carrying out this method, as illustrated in FIGS. 4 and 5 and further described below. Generally, the method can include determining a subject's level of mental fatigue and/or attentional workload by measuring the subject's microsaccade dynamics with as a function of time and/or task complexity and comparing those dynamics to a baseline measure. More specifically, as shown in FIG. 3, baseline microsaccade dynamics can be measured or obtained [process block 14]. Microsaccade dynamics can include microsaccade main sequence, for example microsaccade peak velocity and magnitude. These dynamics can be measured by monitoring eye movements and detecting microsaccades from eye position traces, as discussed below. In terms of measuring baseline dynamics, this baseline measurement can be performed, for example, with respect to an initial time period or an initial/basic task complexity. In other cases, a global baseline measure of microsaccade dynamics can be obtained. In such cases, process block 14 involves obtaining or retrieving this global baseline measure. In addition, in some embodiments, microsaccade dynamics can also include parameters related to drift periods between microsaccades, such as drift speed, etc.

As described in U.S. Pat. No. 7,857,452, the entire contents of which are incorporated herein by reference, eye movements can be monitored non-invasively to measure microsaccade dynamics. Generally, these detection methods include tracking a subject's eye position and detecting microsaccades from eye position traces. Example algorithms for detecting microsaccades objectively from eye position traces (e.g., from video, eye coil, optical, or other suitable tracking methods) include the Martinez-Conde and Macknik algorithm (Martinez-Conde S., Macknik S. L., Hubel D. H. (2000) Nature Neuroscience, incorporated herein by reference) and the Engbert algorithm (Engbert R., Kliegl R. (2003) Vision Res 4:1035-1045, incorporated herein by reference). As discussed above, microsaccades are involuntary movements that cannot be "faked" by a subject.

Referring back to FIG. 3, the method can further include measuring the subject's current microsaccade dynamics with respect to a particular variable, such as time-on-task or task complexity [process block 16]. The current microsaccade dynamics can then be compared to the baseline microsaccade dynamics, for example by calculating slopes of the regression line fitting main sequence populations (with respect to peak velocity as a function of saccadic amplitude) of baseline microsaccade dynamics and current microsaccade dynamics and comparing these slopes [process block 18]. This comparison can then be assessed to determine a level of workload or mental fatigue of the subject based on the particular variable [process block 20]. This assessment can include, for example, calculating a percent decrease of the current microsaccade peak velocity from the basline microsaccade peak velocity. In another example, this assessment can include a determination whether current microsaccade peak velocity has significantly dropped from baseline microsaccade peak velocity, or dropped below a specific threshold. The results of the assessment can then be generated and stored and/or reported (for example, to the subject or another user) [process block 22]. These results can include, for example, the actual percent decrease, an indication whether the decrease is significant (such as a yes/no result), and/or any other indication of the level of mental fatigue and/or attentional workload of the subject based on the assessment. In addition, this method can be repeated after a particular change with respect to the variable, such as a longer time period after time-on-task, a new task with increased complexity has been introduced to the subject, etc. Thus, the method can indicate objective progressive results from multiple time-on-task durations or multiple tasks of differing complexities.

Referring now to FIG. 4, a system 24 for detecting and analyzing eye movement of a subject 25 to measure fatigue and/or mental workload of the subject 25 is presented. The system 24 can include a host 26 operably connected to an eye tracking device 28, a display 30, and a user interface 32. The host 26 can include one or more processors 34 operating under control of one or more computer programs 36 loaded from a non-transitory computer readable medium (memory) 38. As used herein, reference to a step performed by a computer program 36 is also a reference to the processor 34 that performed that step, for example in accordance with the process blocks discussed above. Example tracking devices 28 for use with the present invention can include the EyeLink II by SR Research or other equivalent eye tracking systems such as the IVIEW™ HI-SPEED 1250 tracking system by SensoMotoric Instruments.

The system 24 can operate by presenting a task to the subject 25 through the display 30. For example, one of the processors 34, such as a display processor, can retrieve one or more stored image or video files 40 from memory 38 and present the images/videos to the subject on the display 30, for example mimicking a task. As the images/videos are presented to the subject 25, the eye tracking device 28 can detect the position and movement of the subject's eyes 42. The measurement of microsaccade dynamics and analysis of microsaccade dynamics, such as comparisons of microsaccade peak velocity to a baseline measure (that is, for example, stored in a file 44), as described above, can be executed by one of the processors 34.

In addition, the subject 25 can provide user input through the user interface 32. This user input can be analyzed in conjunction with the task being presented, for example to secondary input for assessing fatigue and/or workload capacity. Furthermore, reports, such as those described above with respect to FIG. 3, can be generated, stored in the memory 38 (within one or more files 44), and/or displayed (via the display 30 or a different display). Accordingly, the system of FIG. 4 can be used to perform the method described above for detecting and analyzing eye movement of a subject to measure a level of fatigue and/or workload capacity of the subject 25. In some applications, the system of FIG. 4 can be used to generate reporting data for use in preparing the baseline microsaccade peak velocity and/or other thresholds, as further described below.

In some applications, as shown in FIG. 5, a system 24 of the present invention can include an eye tracking device 28 and a host 26 with one or more processors 34 and memory 38 including one or more stored computer programs 36 and/or files 44. The system of FIG. 5 can be used to monitor eye movements to determine level of fatigue and/or mental workload in response to outside tasks (that is, tasks not generated by the host 26). As a result, the system of FIG. 5 can be used to continuously monitor the subject from a standoff distance, for example without the subject's knowledge, to determine the subject's level of fatigue and/or mental workload. For example, the subject's microsaccade dynamics can be measured and recorded continuously throughout the subject's workday at their workstation. This recorded data can then be assessed to indicate periods at which the subject's level of fatigue drops below threshold levels.

By way of example, a specific application for methods and systems of the present invention includes measuring mental fatigue and task complexity in air traffic controllers. Air traffic controllers are responsible for monitoring the airspace and separation between aircraft. Their primary purpose is to prevent collisions and conflicts by keeping the positions of aircraft at safe distances from one another. Typically, air traffic controllers use radars to assess current and future aircraft positions based on aircraft location, speed, wind speed, etc. Air traffic control mistakes can cost human lives and money, so it is important to assess the attentional state of air traffic control staff. This problem has been studied extensively, but to date nobody has examined the role air traffic control mental fatigue and task complexity on the main sequence of microsaccades. It is well known that the decisions and plans of an air traffic controller are influenced by factors such as sector complexity, traffic density, vigilance, and the arousal state of the operator. For example, traffic density has been recognized as one of the top five categories that lead to poor performance of air traffic controllers (Durso and Manning, 2008).

Currently, self-report is the only assessment parameter for determining mental fatigue and/or task complexity of air traffic controllers. There is also some testing of reaction-time in certain groups (air traffic controllers, pilots, etc.) before entering a demanding environment, though the subject knows the testing is happening and can prepare for it. Methods of the present invention, however, can provide an objective measure of mental fatigue and/or task complexity, as microsaccades are involuntary movements. Furthermore, the methods of the present invention can be performed either continuously, without the subject's knowledge and without pulling them away from their demanding task (for example, using the system of FIG. 5), or it can be used in a formal testing environment to assess mental fatigue and workload (for example, using the system of FIG. 4). More specifically, with respect to the continuous or secret measurements, the methods can be performed noninvasively by measuring involuntary and unconscious eye movements that occur in virtually every viewing condition, and so the subject need not even know when they are being assessed. Thus, methods of the present invention can be used to objectively assess subject readiness to enter, or continue within, a demanding working environment. This can be applied to air traffic controllers, as well as pilots, surgeons, etc.

Figure 6A:
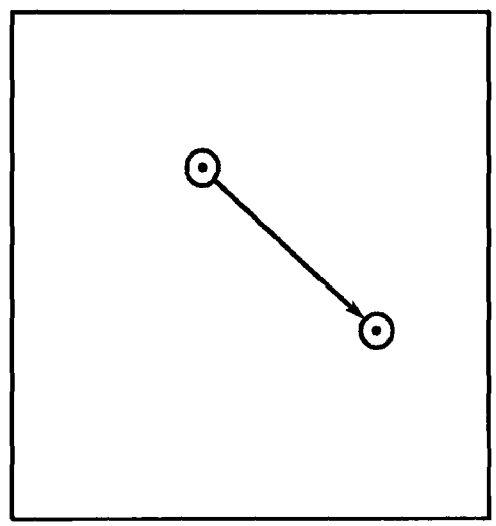
FIG. 6a is a representation of a moving saccade across a display.
Figure 6B:
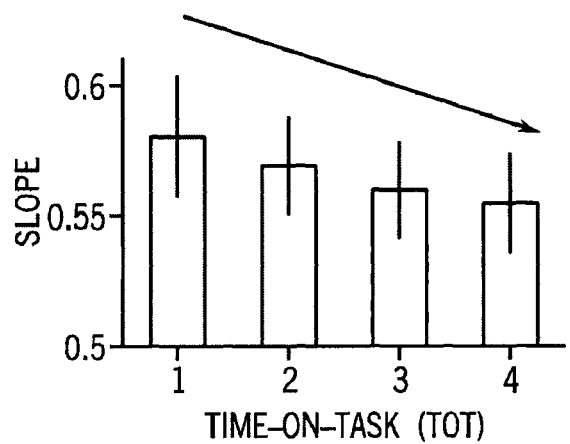
Figure 6C:
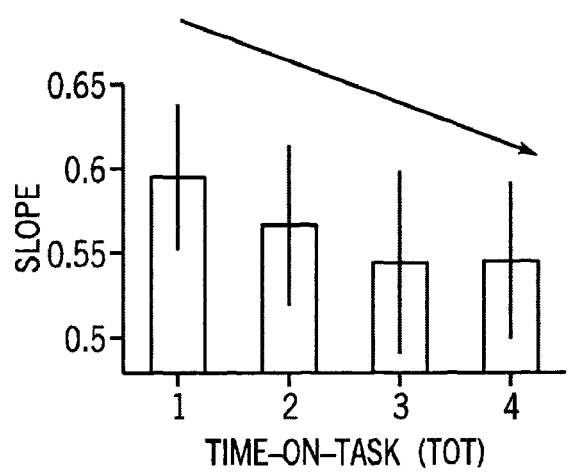

A preliminary study assessing the feasibility of the present invention was performed by monitoring subjects performing guided viewing on an image to determine fatigue as a function of time-on-task. More specifically, the subject's saccades were guided by a pseudorandomly bouncing fixation point around a display (as shown in FIG. 6a) for four thirty-minute trials. The pseudorandom bouncing fixation point ensured that saccade size distributions remained the same across the four thirty-minute trials. Microsaccade dynamics were monitored and analyzed during the trials. FIG. 6b illustrates a slope of peak velocity as a function of saccade size main sequence for each trial. FIG. 6c illustrates a slope of peak velocity as a function of microsaccade size main sequence for each trial. As shown in FIGS. 6b and 6c, both saccade and microsaccade main sequence slopes significantly degrade as a function of time-on-task. These results illustrate that both saccade dynamics and microsaccade dynamics are suitable to monitoring mental state variations in visual search tasks, such as for the examples described above.

For example, with further reference to air traffic controllers, subjects viewing a radar can be assessed through simulated tasks. The number of aircraft on the radar can be manipulated to change task complexity and simulations can be run over an approximate eight hour time period (to assess mental fatigue over a time-period equivalent to a typical daily work period) to induce different states of attention among the participants and analyze (micro)saccade behavior across time and task complexity levels. More specifically, subjects can perform an initial air traffic controller task in which the subjects will judge whether any two triangles, presented on a five-ring "radar" screen, are in conflict, defined as when two triangles on the same ring have the same color. By comparing the main sequence dynamics between complex and easy versions of these tasks, the role of complexity in degradation in the main sequence can be determined. These conditions, each presented in 3-second trials, can be randomly interleaved into 13 thirty-minute time-on-task sequential bins of results, thus imitating a typical eight hour day with an hour lunch break and two fifteen-minute coffee breaks. Three control tasks can be randomly interleaved, in which the subject will either freeview or fixate a radar screen, or perform guided viewing over a radar screen. These control conditions can measure the effects of mental fatigue in isolation from complexity as there will be no task to perform. In the free viewing tasks, subjects will have full control over their eye position and will do the simulated air traffic control task (to detect two like-colored triangles when positioned within the same ring of the radar). In the fixation task, the subjects will do the same task while fixated at the center of the screen. Either way, the subjects' task can be made easy (low number of distracters) or complex (high number of distracters).

Data from the study examples discussed above can be further used in conjunction with well-established tests of fatigue and complexity. Thus, the significance of the data, such as percent decreases from baseline, can be directly related to well-established assessment parameters to determine thresholds for use with the present invention. More specifically, if data illustrating a specific percent drop from baseline coincides with a signification level of fatigue, as determined through other well-established tests, this percentage can be used as a stored threshold for use in later assessments using the present invention. As a result, reports indicating accurate levels of fatigue and/or mental workload can be generated through eye movement monitoring with respect to a baseline value and predetermined fatigue and/or workload thresholds.

Thus, eye movement parameters such as (micro)saccadic peak velocity can serve as indicators of mental fatigue and/or mental workload. These valuable fixational eye movements occur not only during prolonged fixation, but also in the intersaccadic fixation periods during normal visual exploration. As a result, it is possible to monitor eye movement indices of mental fatigue while subjects are involved in their duty, without the need for artificial oculomotor tests currently in use, such as the guided saccade task. Continuous on-line eye-movement based evaluation of subjects, such as ATC operators, could improve safety and efficiency, and reduce operational costs.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for determining a subject's level of fatigue, the method comprising the steps of:
   obtaining, by a host device in electrical communication with an eye tracking device and storing baseline microsaccade peak velocities and microsaccade magnitudes, recorded data comprising recordings of eye movements of the subject recorded as the subject is performing one or more tasks, the recordings being recorded during a gaze fixation of the subject;
   measuring, by the host device from the eye movements represented by the recorded data, microsaccadic eye movement dynamics of the subject, the microsaccadic eye movement being an involuntary eye movement occurring during the gaze fixation;
   calculating, by the host device, current microsaccade peak velocities and microsaccade magnitudes from the measured microsaccadic eye movement dynamics;
   calculating, by the host device, a current slope of the current microsaccade peak velocities as a function of microsaccade magnitude and calculating a baseline slope of the baseline microsaccade peak velocities as a function of microsaccade magnitude;
   comparing, by the host device, the current slope of the microsaccade peak velocities to the baseline slope of the microsaccade peak velocities;
   determining, by the host device, the level of fatigue based on a difference between the current slope and the baseline slope using the recorded data obtained from the eye tracking device; and
   generating a report, by the host device, indicating the level of fatigue based on the recorded data obtained from the eye tracking device.

2. The method of claim 1, wherein generating the report comprises including in the report one of a percent decrease of the current microsaccade peak velocities from the baseline microsaccade peak velocities, an indication that current microsaccade peak velocities significantly decreases from the baseline microsaccade peak velocities, and an indication that current microsaccade peak velocities decreases from the baseline microsaccade peak velocities past a threshold value.

3. A system for indicating a subject's level of fatigue, the system comprising:
   a host device having a processor and memory and receiving recorded data from an eye tracking device comprising eye movements of the subject during gaze fixation recorded as the subject is performing one or more tasks;
   the memory storing program instructions;
   the processor executing the program instructions to:
      obtain baseline microsaccade peak velocities and microsaccade magnitudes representing eye movements of an individual that is not fatigued;
      measure, from the recorded data, microsaccadic eye movement dynamics of the subject, the microsaccadic eye movement being an involuntary eye movement occurring during the gaze fixation;
      determine, using the microsaccadic eye movement dynamics of the subject, current microsaccade peak velocities and microsaccade magnitudes;
      compare a current slope of the current microsaccade peak velocities as a function of microsaccade magnitude to a baseline slope of the baseline microsaccade peak velocities as a function of microsaccade magnitude;
      determine, as the subject's level of fatigue, a level of fatigue associated with the comparison; and
      generate a report to a user of the system, the report based on the recorded data received from the eye tracking device and indicating the subject's level of fatigue.

4. The system of claim 3, wherein the memory further stores the baseline microsaccade peak velocities and microsaccade magnitudes and the processor obtains the baseline peak velocities and microsaccade magnitudes by retrieving the baseline peak velocities from the memory.

5. The system of claim 3, wherein the baseline microsaccade peak velocities and microsaccade magnitudes are recorded from the subject before the subject begins performing the one or more tasks.

6. The system of claim 3, wherein the host device further comprises a display, and wherein the processor further executes the program instructions to present the one or more tasks to the subject on the display.

7. The system of claim 3, wherein the one or more tasks are outside tasks not generated by the system.

8. The system of claim 3, wherein the host device receives the recorded data as the recorded data is recorded, and wherein the processor executes the program instructions substantially contemporaneously with the host device receiving the recorded data.

9. The system of claim 8, wherein the recorded data is recorded continuously as the subject performs the one or more tasks, and the processor generates the report in real-time.

10. The system of claim 3, wherein the processor further executes the program instructions to:
  obtain a baseline slope representing a first regression of peak microsaccade velocities as a function of time-on-task for the individual that is not fatigued;
  calculate, from the microsaccadic eye movement dynamics of the subject, a current slope representing a second regression of peak microsaccade velocities as a function of time-on-task for the subject, the second regression ending at a current time-on-task corresponding to the current peak microsaccade velocities; and
  compare the current slope to the baseline slope to produce a slope difference;
  wherein the level of fatigue determined as the subject's level of fatigue is further associated with the slope difference.

11. The system of claim 1, wherein the eye tracking device and the host device cooperate to record the eye movements of the subject and determine, using the microsaccadic eye movement dynamics, the subject's level of fatigue at a standoff distance from the subject.

12. A system for determining a subject's level of fatigue, the system comprising:
  an eye tracking device positioned in an environment of the subject to monitor the subject's eyes during one or more tasks;
  a host device operatively connected to the eye tracking device, the host device having a processor and memory and receiving recorded data comprising eye movements of the subject during gaze fixation recorded as the subject is performing one or more tasks;
  the memory storing program instructions and a baseline value for a slope of microsaccade peak velocity as a function of microsaccade magnitude; and
  the processor executing the program instructions to:
    measure, from the recorded data, microsaccadic eye movement dynamics of the subject, the microsaccadic eye movement being an involuntary eye movement occurring during the gaze fixation;
    determine, using the microsaccadic eye movement dynamics of the subject, current microsaccade peak velocities and microsaccade magnitudes;
    determine that a current slope representing current microsaccade peak velocities as a function of microsaccade magnitude is less than the baseline value; and
    generate an indication, based on the recorded data received from the eye tracking device, to a user of the system that the subject is fatigued.

13. The system of claim 12, wherein the host device controls the eye tracking device to record the recorded data, and receives the recorded data from the eye tracking device.

14. The system of claim 12, wherein the baseline value is associated with a readiness of the subject to perform the one or more tasks, and the indication that the subject is fatigued further indicates that the subject is not ready to either enter or to continue working in the environment.

* * * * *